United States Patent [19]

Tesmann et al.

[11] 4,255,450
[45] Mar. 10, 1981

[54] USE OF AMINOHYDROXY ACID AMIDES AS ANTIMICROBIAL SUBSTANCES

[75] Inventors: Holger Tesmann, Düsseldorf; Horst Rutzen, Langenfeld; Frau E. Börner, Düsseldorf, all of Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 42,793

[22] Filed: May 29, 1979

[30] Foreign Application Priority Data

May 31, 1978 [DE] Fed. Rep. of Germany ....... 2823685

[51] Int. Cl.³ .................... A01N 37/18; A61K 31/16
[52] U.S. Cl. ................................................ 424/320
[58] Field of Search ........................................ 424/320

[56] References Cited
FOREIGN PATENT DOCUMENTS 2734596 2/1979 Fed. Rep. of Germany .

Primary Examiner—Leonard Schenkman

Attorney, Agent, or Firm—Hammond & Littell, Weissenberger and Muserlian

[57] ABSTRACT

The method for reducing microbial activity which comprises administering an effective amount of aminohydroxy stearic acid amides of the formula

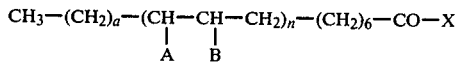

wherein $n=1$ and $a=7$, $n=2$ and $a=4$, or $n=3$ and $a=1$ and wherein one of A and B represents a hydroxyl group and the other of A and B, and X, each represent a radical of the formula

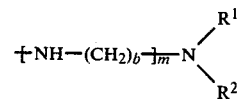

wherein b is an integer of from 2 to 6, m is 1 or 2, and $R^1$ and $R^2$ each independently represent hydrogen or an alkyl radical having from about 1 to 12 carbon atoms.

5 Claims, No Drawings

USE OF AMINOHYDROXY ACID AMIDES AS ANTIMICROBIAL SUBSTANCES

BACKGROUND OF THE INVENTION

This invention is directed to reducing microbial activity. More particularly, this invention is directed to reducing microbial activity by administering aminohydroxy stearic acid amides.

OBJECTS OF THE INVENTION

It is an object of this invention to provide a method for reducing microbial activity.

It is also an object of the invention to provide a method of administering aminohydroxy stearic acid amides to reduce microbial activity.

These and other objects of the invention will become more apparent in the disclosure below.

DETAILED DESCRIPTION OF THE INVENTION

This invention is directed to the use of aminohydroxy stearic acid amides where amino and hydroxy groupings are arranged in vicinal position on the alkyl chain, as antimicrobial substances. It has been found that aminohydroxy stearic acid amides of the formula

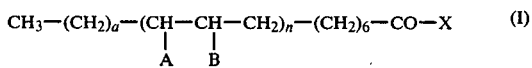

wherein n=1 and a=7, n=2 and a=4, or n=3 and a=1 and wherein one of A and B is a hydroxy group, while the other of A and B, and X, each represent a radical of the formula

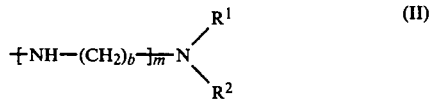

wherein b is an integer of from 2 to 6, m is 1 or 2, and $R^1$ and $R^2$ each independently represent hydrogen or an alkyl radical having from about 1 to 12 carbon atoms, can be used with excellent results as antimicrobial substances.

The compounds of Formula I can be produced by known methods. Preferably they are produced according to the method described in German published patent application P 27 34 596.6 by reacting epoxy-stearic esters of the formula

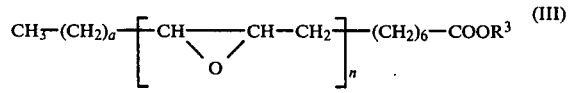

with di- and triamines of the formula

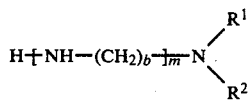

wherein a, b, m, n, $R^1$ and $R^2$ have the same meanings as in Formulas I and II, and wherein $R^3$ represents an alkyl radical having from about 1 to 5 carbon atoms or the radical of a polyvalent alcohol having from about 2 to 6 carbon atoms whose other hydroxyl groups are likewise esterified with epoxy fatty acid esters or, if necessary, also with saturated and unsaturated fatty acid esters. The epoxy stearic acid esters of Formula III are reacted with at least n+1 moles of an amine of Formula IV, if necessary, in the presence of a polar solvent at temperatures of from about 130° to 200° C. Volatile byproducts are separated after the reaction is completed.

If the epoxy stearic acid esters of Formula III are reacted with the amines of Formula IV in a solvent, a lower alkanol, such as methanol, ethanol, or isopropanol, as well as ethylene glycol or glycerin, is particularly suitable for this purpose. These alcohols can also be mixed with water. The addition of catalytic amounts of an alkali, such as sodium hydroxide, is also advisable.

In the epoxy stearic acid esters of Formula III, the acid component consists of epoxidized oleic acid, linoleic acid, or linolenic acid, that is, of epoxidized fatty acids having a $C_{18}$ chain length. The above mentioned acids each also contain, depending on their source, portions of unsaturated $C_{14}$, $C_{16}$, $C_{20}$, or $C_{22}$ fatty acids in minor quantities of up to a total of 25% by weight. Because of their easy accessibility, the epoxy esters of Formula III, which can be derived from oleic acid found in many natural fats, are of particular practical interest for the preparation of the compounds used according to this invention.

The alcohol component of the compounds of Formula III consists of lower aliphatic alcohols, such as methanol, ethanol, propanol, isopropanol, n-butanol and n-pentanol, or of aliphatic di- and polyols, such as ethylene glycol, propylene glycol, 1,6-hexanediol, and glycerin.

Epoxidized fatty acid esters of monovalent alcohols having from about 1 to 5 carbon atoms, particularly the methyl esters, are useful as esters of Formula III for the production of the compounds of Formula I. If the compounds of Formula I are produced from epoxidized esters of polyvalent alcohols, which are readily available from natural fatty acids, then triglycerides, glycerin, or fatty acid partial glycerides may still be contained in the reaction product. However, the beneficial effect of the products is not significantly impaired. The fatty acid derivatives of saturated or unsaturated fatty acids obtained as byproducts are those which have from about 10 to 22, expecially from about 12 to 18, carbon atoms.

Thus, it is not necessary to use the pure oleic, linoleic, and linolenic acid esters to provide the basic structure of the epoxy compounds of Formula III. Rather, epoxidized fatty acid ester mixtures can be used as starting materials, such as are obtained from natural vegetable and animal fats, including olive oil, soybean oil, rape oil, cottonseed oil, linseed oil, tallow, fish oils, tallow oil, and the like. The amines of Formula IV are aliphatic diamines and triamines, such as ethylene diamine, trimethylene diamine, tetramethylene diamine, pentamethylene-diamine, hexamethylene diamine, diethylene triamine, and di-trimethylene triamine, as well as their unsymmetrically substituted mono- and dialkyl derivatives, such as N,N-dimethylaminoethylene amine, N,N-dimethylaminopropyl amine, and N-dodecylaminopropylamine.

In the production of the compounds of Formula I, preferably an epoxy stearic acid ester of a monovalent $C_1$ to $C_3$ alcohol is reacted with from 2 to 10 moles of an amine of Formula IV. The reaction is typically carried out at a temperature of from about 130° to 160° C. in a polar solvent selected from the group of the monovalent, bivalent, or trivalent alcohols having from 1 to 3 carbon atoms. A catalytic amount of alkali, such as sodium hydroxide solution, may be present. The reaction time is generally from about 2 to 12 hours. The reaction is considered complete when practically no epoxy groups can be detected. In the treatment of the reaction mixture, the product is separated from the volatile ingredients, that is, from the solvents and from the amine of Formula IV used in excess. The separation is generally effected by distillation or by washing with a saturated aqueous salt solution, for example, with a sodium chloride, sodium carbonate, or sodium sulfate solution.

The compounds to be used according to this invention include, for example, the reaction products of epoxy stearic acid methylester with ethylene diamine, that is, a mixture of N-(2-aminoethyl)-amides of 9-(2-aminoethyl)-10-hydroxy-stearic acid and of 10-(2-aminoethyl)-9-hydroxy-stearic acid. Also included are the corresponding aminohydroxy stearic acid amides obtained by reacting epoxy stearic acid methylester with trimethylene diamine, tetramethylene diamine, pentamethylene diamine, hexamethylene diamine, diethylene triamine, N-methylethylene diamine, N,N-dimethyl-aminopropylamine, or N-dodecylaminopropylamine. Further useful compounds include the reaction product of epoxidized olive oil fatty acid methyl ester with trimethylene diamine; the reaction product of epoxidized tall oil fatty acid with N,N-dimethylethylene diamine; the reaction product of the mixture of 50% by weight epoxidized tallow fatty acid methyl ester and 50% by weight epoxidized soybean fatty acid methyl ester with hexamethylene diamine; the reaction product of the mixture of 70% by weight epoxidized soybean fatty acid methyl ester and 30% by weight epoxidized fish oil fatty acid methyl ester with di- or trimethylene triamine; and the reaction product of epoxidized olive oil with ethylene diamine.

For use as antimicrobial agents, the aminohydroxy stearic acid amides can be incorporated into liquid, pasty or solid preparations, for example, in aqueous solutions, suspensions, emulsions, and solutions in organic solvents. These antimicrobial compositions can be used in various fields, for example, as cleansers disinfectants, and preservatives for textiles, floors, hospital equipment or instruments, and commercial installations, such as dairies, breweries and laundries. The aminohydroxyl stearic acid amides are used in amounts of from about 0.1 to 10% by weight, preferably from about 0.5 to 5% by weight, based on the total weight of the composition.

In addition, the aminohydroxy stearic acid amides can be used in the preservation of technical products which are subject to the attack by bacteria and fungi or other microbial destruction, such as starch pastes, glues, and dispersion dyes, as well as cutting and drilling oils. For these purposes, an addition of from about 0.1 to 2% by weight, based on the total weight of the material to be preserved, is generally sufficient.

EXAMPLES

The following examples describe the subject of the invention more fully and are not intended to limit the invention to these examples.

I. Preparation of the aminohydroxy stearic acid amides

EXAMPLE 1

Reaction product of epoxy stearic acid methyl ester and ethylene diamine.

(Product A)

A mixture of 66.8 g (0.21 mole) epoxy stearic acid methyl ester (4.78% by weight epoxy oxygen), 60.1 g (0.77 mole) ethylene diamine, 200 ml methanol, and 80 ml water was heated in an autoclave to 130° C. and kept at that temperature for 12 hours. After cooling, the reaction solution was filtered, the filtrate was concentrated, and excess ethylene diamine was distilled off under reduced pressure. The reaction product was a brownish, viscous mass. Index of refraction $n_D^{25}$ 1.3720 (25% by weight solution in methanol).

EXAMPLE 2

Reaction product of epoxy stearic acid methyl ester and hexamethylene diamine.

(Product B)

A mixture of 78 g (0.25 mole) epoxy stearic acid methyl ester (4.57% by weight epoxide oxygen), 73 g (0.63 mole) hexamethylene diamine, and 120 ml methanol was heated in an autoclave to 200° C. and kept at that temperature for 8 hours. After cooling, the product was filtered, and the solvent and excess hexamethylene diamine were distilled off from the filtrate under reduced pressure. A yellow-orange viscous mass remained as the reaction product. Index of refraction $n_D^{25}$ 1.3705 (25% by weight solution in methanol).

EXAMPLE 3

Reaction product of epoxy stearic acid methyl ester and di-trimethylene diamine.

(Product C)

A mixture of 62.5 g (0.2 mole) epoxy stearic acid methyl ester (4.57% by weight epoxy oxygen), 65 g (0.5 mole) di-trimethylene triamine, and 100 ml methanol was heated in an autoclave for 6 hours to 160° C. After filtration and evaporation of the filtrate under reduced pressure, the reaction product was obtained as a brownish paste. Index of refraction $n_D^{25}$ 1.3760 (25% by weight solution in methanol).

EXAMPLE 4

Reaction product of epoxy stearic acid methyl ester and N,N-dimethyl propylene diamine.

(Product D)

A mixture of 147.5 g (1.45 mole) N,N-dimethyl propylene diamine and 32.5 g glycerin was heated to 130° C., and 85 g (0.27 mole) epoxy stearic acid methyl ester (4.41% by weight epoxy oxygen) were added in drops under stirring. The mixture was stirred for another 3 hours at 130° C. Then the volatile components were distilled off at a bath temperature of 160° to 185° C. under oil pump vacuum (0.01 torr). A yellow-brown paste was obtained as a reaction product. Index of refraction $n_D^{25}$ 1.3652 (25% by weight solution in methanol).

EXAMPLE 5

Reaction product of epoxy stearic acid methyl ester and N-dodecylpropylene diamine.

(Product E)

An amount of epoxy stearic acid methyl ester, 133 g (0.43 mole; 4.57 by weight epoxy oxygen), 230 g (0.95 mole) N-dodecyltrimethylene diamine, and 700 ml methanol were heated in the autoclave to 180° C. and kept at that temperature for 8 hours. After cooling, the product was filtered. The volatile portions were distilled from the filtrate under reduced pressure and a brown paste was obtained as a reaction product. Index of refraction $n_D^{25}$ 1.3658 (25% by weight solution in methanol).

II. Antimicrobial action of the aminohydroxy stearic acid amides

EXAMPLE 6

The antimicrobial action of Products A to E from Examples 1 to 5, respectively, was determined relative to the following test microorganism suspensions:
(1) Staphylococcus aureus $5 \times 10^7$ microorganisms/ml
(2) Escherichia coli $5 \times 10^7$ microorganisms/ml
(3) Pseudomonas aeroginosa $5 \times 10^7$ microorganisms/ml
(4) Candida albicans $5 \times 10^7$ microorganisms/ml The inhibition concentrations of the products to be tested were determined by means of the dilution test according to the guidelines for testing chemical disinfectants of the German Society for Hygiene and Microbiology (1959). The tests were carried out in test tubes which contained standard I-bouillon (Merck) or beer wort (8 deg.BG). After the addition of active ingredients, the volume of the nutrient solution in the tubes was 10 ml each. Subsequently, a 0.1 ml test microorganism suspension of the indicated concentration was placed in the tube. The nutrient solution specimens inoculated with bacteria were stored for 3 days at 37° C. in an incubator. The specimens inoculated with Candida albicans were incubated for 3 days at 30° C. Then it was determined which concentration of the active ingredient added to the nutrient medium had just inhibited the growth of the microorganisms. The value found this way was called the inhibition concentration. The following concentrations of the active ingredients, in ppm, were tested:

1000, 750, 500, 250, 100, 50, 10

For the products A to E the inhibition concentrations, relative to the above mentioned test microorganisms, were as follows:

TABLE 1.

| | Inhibition Concentrations | | | |
|---|---|---|---|---|
| | Inhibition Concentration (ppm) Test Microorganism | | | |
| Product | (1) | (2) | (3) | (4) |
| A | >10 | 50 | 50 | 50 |
| B | >10 | 10 | 50 | 10 |
| C | >10 | 50 | 50 | 50 |
| D | 50 | 100 | 250 | 250 |
| E | >10 | 50 | 250 | 100 |

EXAMPLE 7

The microbicidal action of Products A to E from Examples 1 to 5, respectively, was determined relative to the following test microorganism suspensions:
(1) Staphylococcus aureus $2 \times 10^8$ microorganisms/ml
(2) Escherichia coli $3 \times 10^8$ microorganisms/ml
(3) Pseudomonas aeruginosa $2 \times 10^8$ microorganisms/ml
(4) Candida albicans $8 \times 10^7$ microorganisms/ml The eradication, i.e., killing, times for the products tested was determined by means of the suspension test according to the guidelines for testing chemical disinfectants of the German Society for Hygiene and Microbiology (1959).

The substances to be tested were first dissolved in some alcohol. Test solutions were prepared from the ethanol solutions by dilution with de-ionized water which contained 500, 250, or 100 ppm active ingredient and a maximum of 1% by weight ethanol.

According to the guidelines, 0.1 ml test microorganisms suspensions were pipetted at room temperature into test tubes, and 10 ml of the above described test solutions were added. After each of 2.5, 5, 10, 20, 40, 60, and 120 minutes a drop of the material was removed from the test tubes by means of a dropper, and inoculated in 10 ml nutrient solution containing 3% Tween 80 and 0.3% lecithin as a deinhibitor. The nutrient solution with the bacteria consisted of 1% by weight standard I bouillon (Merck), in the Candida albicans of 1% by weight beer wort solution. The specimens inoculated with bacteria were incubated at 37° C., those inoculated with Candida albicans at 30° C. After 5 days at the earliest, the cultures were examined macroscopically for growth, and the killing times were determined this way, which are represented in the following table II.

TABLE II.

| Killing Time of Products A to E with Concentrations of 500, 250 and 100 ppm | | | | | |
|---|---|---|---|---|---|
| | Amount | Killing Time (minutes) Test Microorganism | | | |
| Product | (ppm) | (1) | (2) | (3) | (4) |
| A | 500 | 2.5 | 5 | 5 | 5 |
| | 250 | 2.5 | 5 | 5 | 10 |
| | 100 | 2.5 | 20 | 10 | 10 |
| B | 500 | 2.5 | 5 | 2.5 | 5 |
| | 250 | 2.5 | 5 | 2.5 | 5 |
| | 100 | 2.5 | 60 | 2.5 | 10 |
| C | 500 | 2.5 | 5 | 2.5 | 5 |
| | 250 | 2.5 | 5 | 2.5 | 10 |
| | 100 | 2.5 | 10 | 2.5 | 20 |
| D | 500 | 2.5 | 10 | 10 | 2.5 |
| | 250 | 5 | 10 | 10 | 2.5 |
| | 100 | 10 | 40 | 10 | 2.5 |
| E | 500 | 10 | 20 | 120 | 2.5 |
| | 250 | 20 | 40 | 120 | 5 |
| | 100 | 40 | 40 | >120 | 40 |

III. Use as an antimicrobial agent

Following are a few examples for the use of the aminohydroxy stearic acid amines according to the invention as antimicrobial agent.

EXAMPLE 8

Disinfecting hand washing paste.

| Component | Parts by Weight |
|---|---|
| Sodium lauryl sulfate (about 35% wash-active substance) | 52 |
| Coconut fatty acid monoethanol amide | 3 |
| Pumice, finely ground | 43 |
| Product A | 2 |

Product C can be used instead of Product A with equally good results.

EXAMPLE 9

Foam bath

| Component | Parts by Weight |
|---|---|
| Sodium lauryl ether sulfate (27 to 28% by weight wash-active substance) | 70 |
| Coconut fatty acid diethanol amide | 5 |
| Product B | 0.5 |
| Water | 24.5 |

Products A or C can also be employed in place of Product B.

EXAMPLE 10

Deodorant Spray

| Component | Parts by Weight |
|---|---|
| Octyl dodecanol | 10 |
| Perfume | 1 |
| Product D | 2 |
| Ethanol | 87 |
| Propellent gas | 100 |

In this composition Product D can be replaced by Product E.

The above examples are set forth for the purpose of demonstrating the invention herein and are not to be construed as limiting the invention thereto.

We claim:

1. A method for reducing microbial activity which comprises adding to a material subject to microbial contamination an effective amount of an aminohydroxy stearic acid amide of the formula

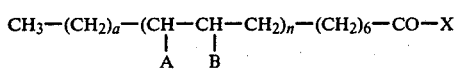

wherein $n=1$ and $a=7$, $n=2$ and $a=4$, or $n=3$ and $a=1$ and wherein one of A and B represents a hydroxyl group and the other of A and B, and X, each represent a radical of the formula

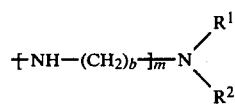

wherein b is an integer of from 2 to 6, m is 1 or 2, and $R^1$ and $R^2$ are each independently hydrogen or an alkyl radical having from about 1 to 12 carbon atoms, or a mixture of said amides.

2. A method for preventing microbial activity in materials to be preserved which comprises adding to said materials an effective amount of an aminohydroxy stearic acid amide as set forth in claim 1.

3. The method of claim 2 wherein an amount of from about 0.1 to 2.0% by weight, based on the weight of the material to be preserved, is added.

4. An antimicrobial composition which comprises an effective antimicrobial amount of aminohydroxy stearic acid amide as set forth in claim 1 and a suitable carrier.

5. An antimicrobial composition of claim 4 which comprises from 0.1 to 10% by weight, based on the total weight of the composition, of aminohydroxy stearic acid amide.

* * * * *